United States Patent [19]

Lynn

[11] Patent Number: 4,946,445
[45] Date of Patent: Aug. 7, 1990

[54] INTRAVENOUS LINE COUPLING DEVICE

[76] Inventor: Lawrence A. Lynn, 862 Curleys Ct., Worthington, Ohio 43085

[21] Appl. No.: 240,539

[22] Filed: Sep. 6, 1988

[51] Int. Cl.$^5$ .............................................. A61M 5/32
[52] U.S. Cl. .................................... 604/192; 604/86; 604/283; 604/905
[58] Field of Search ...................... 604/83, 86, 87, 244, 604/411–414, 905

[56] References Cited

U.S. PATENT DOCUMENTS

| | | | |
|---|---|---|---|
| 3,976,073 | 8/1976 | Quick et al. | 604/414 |
| 4,366,816 | 1/1983 | Bayard et al. | 604/905 |
| 4,432,759 | 2/1984 | Gross et al. | 604/411 |
| 4,588,402 | 5/1986 | Igari | 604/408 |
| 4,636,204 | 1/1987 | Christopherson et al. | 604/283 |
| 4,675,020 | 1/1987 | McPhee | 604/411 |
| 4,752,292 | 6/1988 | Lopez | 604/244 |
| 4,834,716 | 5/1989 | Ogle, II | 604/86 X |

Primary Examiner—Stephen C. Pellegrino
Assistant Examiner—C. Maglione
Attorney, Agent, or Firm—James R. Longacre; Michael L. Keller

[57] ABSTRACT

A medical intravenous line coupling device can be secured to standard "y" shaped junction tube. The device can comprise a single member which fits with the junction tube and has passages shaped to receive and secure with the junction arm. A "b" shaped slot can be provided in the member for that purpose. The container can have a menas for receiving a liquid for injection into the intravenous system, such as a receptacle, and a means for allowing liquid flow from the receiver into the junction tube, such as a needle. The device may include a second member which has a passage to interact with the junction arm. One member can fit about the other and be rotatably mounted hereto. The junction arm can be received by the two members when they are in a first position relative to one another, and can be secured when the members are moved relative to each other. With the two member assembly, the receiver, such as the receptacle, and the liquid flow means, such as the needle, can be mounted to the first or second member. Structure, such as a nib projecting into a slot, can be provided to resist movement of the arm out of a secure relationship. Means, such as an interacting projection and a recess, can hold the two members in the more secure position.

33 Claims, 2 Drawing Sheets

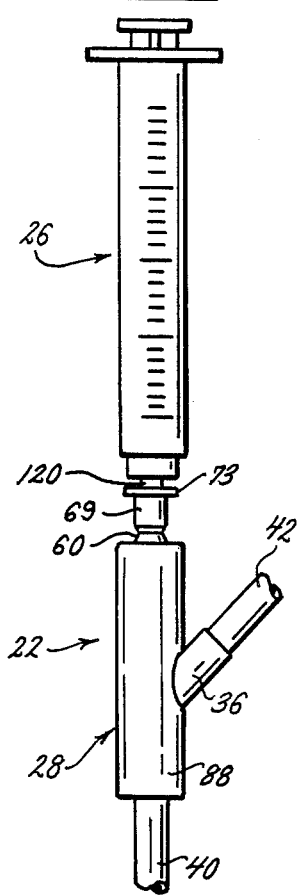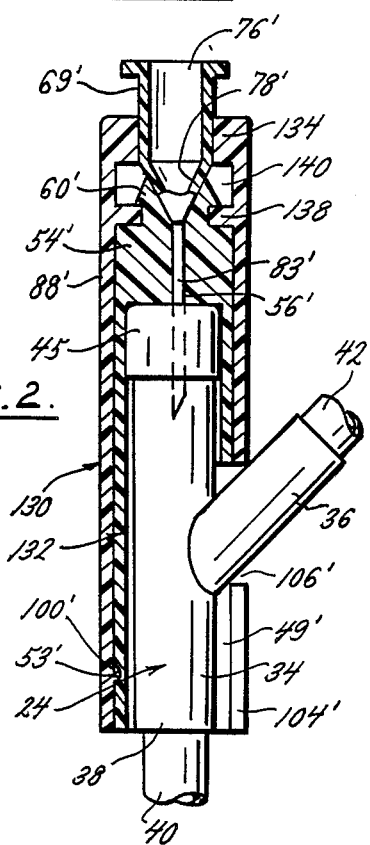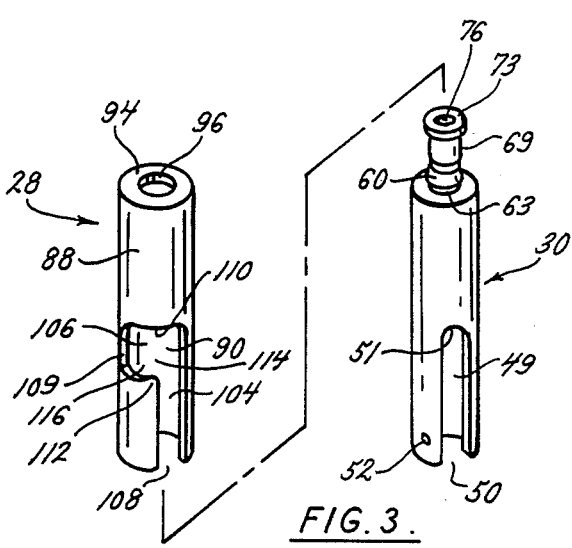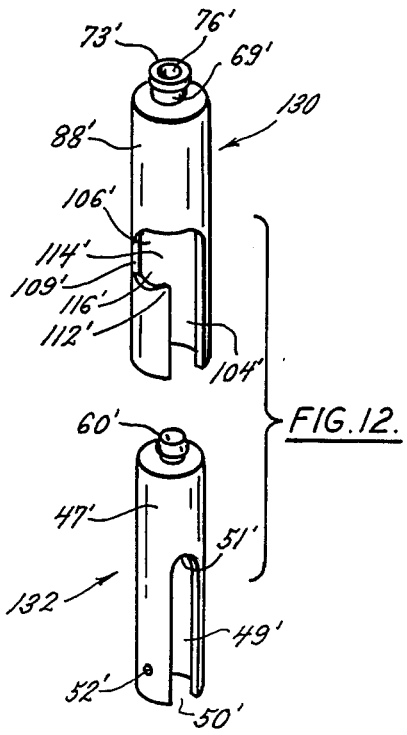

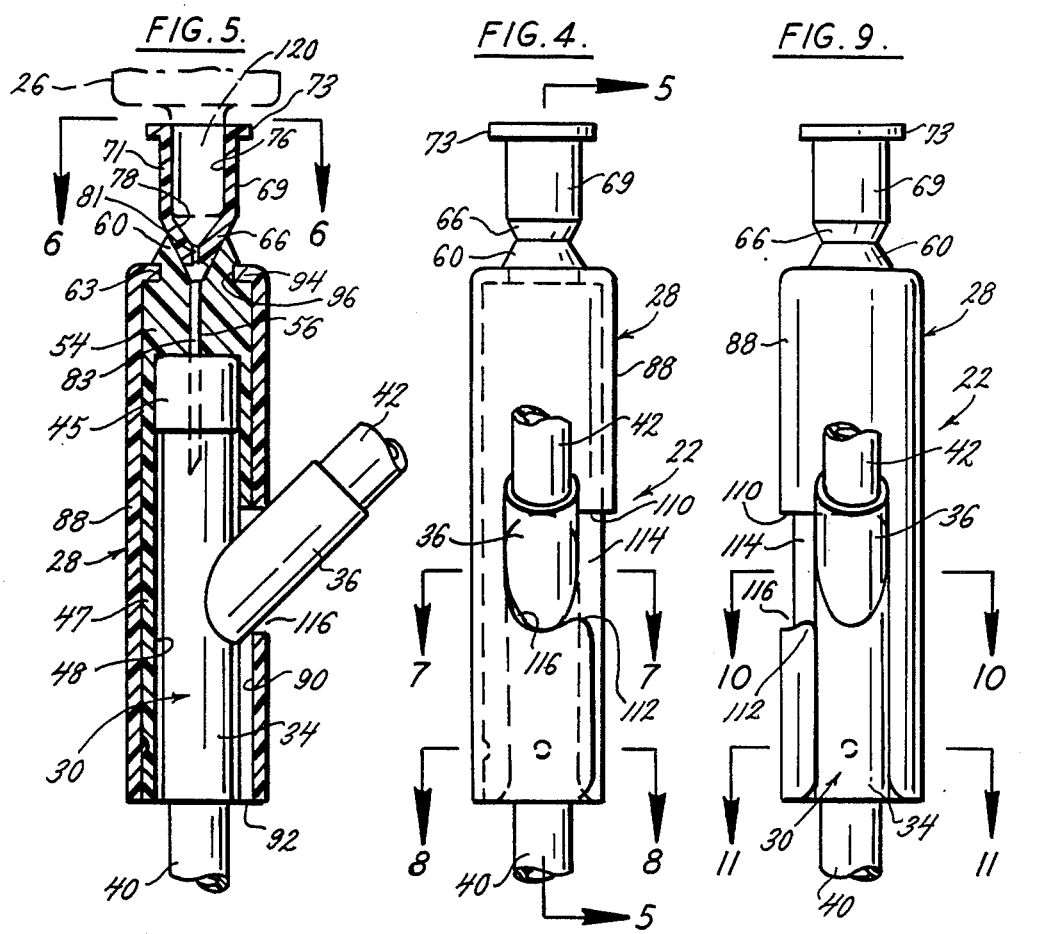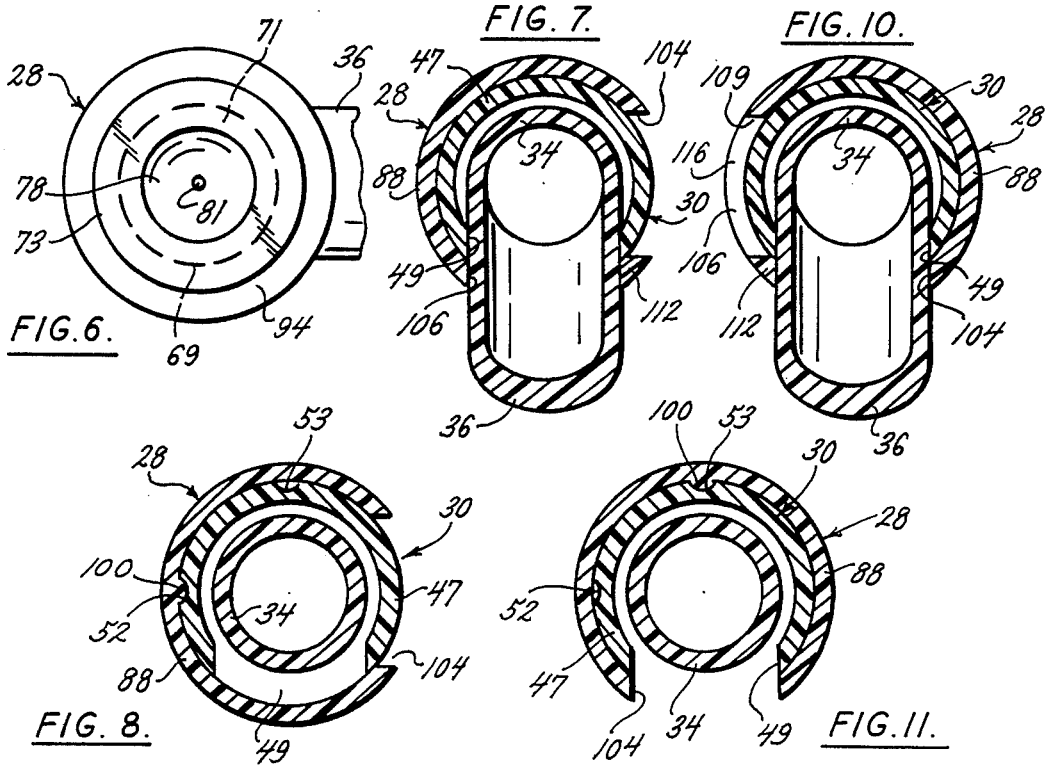

INTRAVENOUS LINE COUPLING DEVICE

BACKGROUND OF THE INVENTION

The attachment of intravenous tubing to intravascular catheters for the administration of fluids and/or medication to patients has been widely utilized for over three decades. Generally, an intravenous tubing system comprises a long segment of tubing which is proximally attached to an elevated bag or bottle of fluid and distally attached to an intravascular catheter. Such a system acts as a primary system, and a secondary conduit may be connected to the primary system. To allow for such connection, such primary systems often have a "y" shaped branch junction section with a penetrable self-sealing septum. A needle attached to the end of the second conduit can be inserted through such a septum to create fluid connection between the primary system and second conduit. Thus, the septum provides a mechanism for the recurrent and frequent connection of secondary, "piggyback" intravenous tubing systems to the primary tubing system. Such second or piggyback systems typically include a small bag of antibiotic or other medication which is dissolved in a fluid and connected to a long flexible plastic conduit. The intermittent connections of such secondary intravenous systems to the primary system allows the administration of the medication at frequent intervals without disconnecting the primary intravenous system and without discontinuing fluid flow through the primary system.

Such "y" shaped tubes typically have a tubular trunk with a cylindrical tubular arm branching from it at an angle which can range from about 30° to 45°. The longitudinal section through such an arm is of elliptical shape. The major axis of this elliptical section varies with the angle of extension of the arm. In particular, the major axis length increases as the angle of arm extension decreases.

A major problem with such systems is that the needles frequently loosen and become disconnected from the septum during fluid administration. This can result in the medication spilling into the patient's bed or on the floor. An even greater problem is that the needle may become contaminated during disconnection. The contaminated needle portion may be readvanced through the septum, thereby introducing contamination into the primary tubing system.

U.S. Pat. No. 4,752,292 discloses a device which helps prevent disconnection of a needle from a compatible interfacing tube having a septum. However, application of this device is limited to tubing systems with specifically compatible interfacing components which fit together. Therefore, the use of that disclosure would require structural changes to the conventional tubing systems which contain septae, and which are deployed in a wide range of existing tubing systems and have long been in use with heterogeneous populations of infusion pumping mechanisms and other devices.

SUMMARY OF THE INVENTION

The invention overcomes problems that exist in the art. The invention comprises a member which can be mounted with the junction tube so that a secure relationship is established with the member and the arm of the "y" shaped junction section or tube to prevent inadvertent removal of the member from the junction tube. The member can have a conduit for extension into liquid flow connection with the junction tube. In an embodiment, the conduit can comprise a needle having a flow channel, with the needle being mounted with the member. When the member is mounted to the junction tube to lock with the arm, the needle can extend within the trunk of the junction tube.

The member further can have means for receiving liquid from the external liquid source. This means can comprise a receptacle associated with the tube which can be integral with the tube, or a separate component mounted with the tube, for example.

The means for establishing a secure relationship between the member and the arm of the junction tube can comprise a slot arrangement permitting insertion of the arm within the slot and movement of the member relative to the junction tube to move the arm into a locking relationship relative to a part of the slot. In an embodiment, the slot can comprise a "b" (lower case) shape having a longitudinal portion and an enlarged transverse portion or hollow slot. The longitudinal portion can have an opening at one end of the member. The member can be of a generally tubular shape.

The member can have a means to resist movement of the member relative to the arm to an unlocked position. This can comprise a projection into the slot to narrow the slot passageway to resist non-volitional movement of the arm relative to the slot. Yet the engagement permits the hand to move the arm to an unlocked position.

The slot portion which receives the arm has a portion of large enough breadth to accommodate receipt of the corresponding portion of the arm therethrough. When the arm is extending at an angle relative to the trunk, the corresponding cross section of the arm is of an elliptical shape. Hence, the slot portion that receives the arm in the locked position is of greater breadth than the major axis of the ellipse.

In an embodiment, the slot arrangement can be generally of a "b" shape on a cylindrical tube. In this embodiment, the width of the longitudinal portion of the slot can be less than the breadth of the transverse slot portion which receives the arm in the locking position.

The invention comprises the single member, although it is believed that a device comprising an ensemble of a first member and a second member is preferred. In the two member arrangement, the invention comprises a device having first member which can be mounted to the junction tube, and a second member which can be mounted with the first member. The first and second members have means for locking with the junction tube arm to prevent movement of the junction tube away from the second member.

One of the first or second members can have a means for receiving a liquid source for administration to a patient, such as from a separate syringe, or from another tube. The device also has means to provide flow of the liquid from the outside source to the junction tube.

In an embodiment of the invention, the first member and second member are both tubes with slots. The slots have parts that can be aligned so that the junction arm can be moved within the slots. One of the tubes has a slot with first and second sections so that the junction arm can be slid through the first slot section, and then the tube can be moved relative to the junction arm to have the second slot section extend about the junction arm. Such positioning blocks movement of the second tube relative to the junction arm in both longitudinal directions, and also blocks movement in a third transverse direction. The slot with two sections can be a general "b" shape. The transverse section of the "b" shaped slot provides an enlarged portion which is sized to accommodate the length of the major axis of the corresponding elliptical cross section of the arm.

Means for holding the arm within the locked position to resist non-volitional movement in the fourth direction can be provided. Such means can comprise a nib projecting from the wall of the second slot section to provide a resistance gate against passage of the arm. The nib can be of resilient material so that it flexes to allow the junction arm to pass to and from the second slot section when the first or second members are rotated by the hand, and likewise allows the junction arm to be rotated out of the second slot when the first or second members are hand rotated. This is also a means of preventing movement of the first and second tubes relative to each other, and of the junction tube relative to the first and second members by non-volitional movement.

When the tubes are rotated in relation to each other, the inner tube will remain in a fixed nonrotational relationship with the arm.

The two members can also have means to releasably engage each other when they are moved to be in a locking engagement with the junction arm, so that non-volitional movement of the first member relative to the second member to move those tubes to an unlocked position is resisted in the fourth direction. In one embodiment, the first and second members can have matching extensions and recesses which interfit to provide such releasable lock. In the embodiment using the tubes, the inner surface of the outer tube can have an extension or a recess which matches with a recess or an extension, respectively, on the outer surface of the inner tube. The tubes can be of resilient material to allow disengagement upon hand movement.

The two members can therefore be locked upon the arm with non-volitional movement being inhibited in all four directions, thereby preventing non-volitional disengagement of the two members from the arm.

The means for receiving a liquid source can be a receptacle located on one of the first or second members. The means for allowing liquid flow from the receptacle to within the junction tube can comprise a needle mounted to the device to pierce the septum on the junction tube. Fluid flow connection is provided between the receptacle and the needle to thus allow liquid flow from the receptacle into the junction tube.

A means for holding the first member against longitudinal movement relative to the second member is also provided. In an embodiment, one member can have a groove such as an annular groove, and the second member can have a projecting component that fits within the groove to allow the first tube to rotate relative to the second tube, but to prevent longitudinal movement of the first member relative to the second member. The projecting component can be an annular rim extending inwardly from the outer tube to fit within an annular groove of the inner tube. The projecting component can be flexible so that it can be enlarged by passage of the projection. In an embodiment a frusto-conical shape connecting member is provided to force flexing of a resilient annular rim, with the rim flexing back to its initial position once it is received within the groove.

It is believed that the two member device provides greater stability and resistance against inadvertent disengagement than the single member arrangement. Further, the two member arrangement provides for stability despite the varying degrees of tightness of fit which results from accommodation of a wide range of angles for the arm relative to the trunk of the junction tube. For example, junction tube arms having smaller angles result in elliptical longitudinal sections having greater lengths of major axes at the intersection of the arm with the hollow. Therefore, such arms would fit only loosely into a hollow which is sized to accommodate junction sections of more acute angles. The addition of a second tube, therefore, provides for much greater stability since it has only a longitudinal slot which receives the branching angle into its longitudinal axis and therefore the required receiving width of the longitudinal slot is not affected by the branching angle. Therefore, a greater universal tightness of fit is secured throughout the conventionally used branching angles by an embodiment which comprises two tubes.

Hence, in addition to the foregoing objects, it is also generally an object of the invention to provide a means for secure connection of a secondary tubing system or fluid source to a "y" shaped junction section of a primary tubing system without significant risk of inadvertent disconnection and contamination, or of accidental needle stick.

It is another object of the invention to provide a device which is completely suitable for use in conjunction with the "y" shaped junction sections deployed in the heterogeneous population of existing tubing systems, and which does not require any additions or changes to the structures of currently existing tubing systems. In particular, it is further the object of this invention to provide a device which can reliably lock onto a variety of conventional "y" shaped branch junction sections having variable branching angles and diameters.

These and other objects of the invention shall become apparent from the following description.

DESCRIPTION OF THE DRAWINGS

FIG. 1 is a front elevation view showing the coupling device mounted to a junction tube, with a syringe connected to the coupling device;

FIG. 2 is an exploded elevation view of the coupling device, showing toward the bottom the inner mount tube, and above the outer mount tube;

FIG. 3 is an offset isometric view showing the outer mount tube and the inner mount tube;

FIG. 4 is an elevation showing the coupling device mounted to the junction tube, with the outer mount tube mounted on the inner mount tube and rotated to the locked position;

FIG. 5 is a section on the Line 5—5 of FIG. 4;

FIG. 6 is a top plan view taken on the Line 6—6 of FIG. 5;

FIG. 7 is a section of the coupling device and junction tube taken on the Line 7—7 of FIG. 4;

FIG. 8 is a section of the coupling device and junction tube taken on the Line 8—8 of FIG. 4;

FIG. 9 is a side elevation showing the coupling device mounted to the junction tube, in the unlocked position;

FIG. 10 is a section of the coupling device and junction tube taken on the Line 10—10 of FIG. 9;

FIG. 11 is a section of the coupling device and mount tube taken on the Line 11—11 of FIG. 9;

FIG. 12 is an exploded isometric view of a modified coupling device having an inner and an outer mount tube; and FIG. 13 is a section view of the modification of FIG. 12 shown mounted to a junction tube.

DESCRIPTION OF A PREFERRED EMBODIMENT

An embodiment of the novel coupling device 22 is shown in FIGS. 1-11. In FIG. 1, the device 22 is shown mounted to a junction tube 24, with a source of fluid for administration to a patient, shown in the form of a syringe 26, being connected to the device 22.

As shown clearly in FIGS. 2 and 3, coupling device 22 comprises an outer mount tube 28 and an inner mount tube 30. The outer tube 28 can be mounted about the inner tube 30, with both tubes extending about the junction tube 24 in the unlocked position, such as depicted in FIG. 9, and in a locked position, such as depicted in FIGS. 1, 4, and 5.

First, for a better understanding of the operation of device 22, the junction tube 24 is described. Junction tube 24 is of the standard "y" shape, as is known in the art. Junction tube 24 has a main tubular trunk 34 with an angular tubular arm 36 integrally secured thereto. Trunk 34 and arm 36 are both hollow and in fluid flow connection with one another. The distal end 38 of trunk 34 receives a flexible plastic tube 40 which extends to a terminal (not shown) for connection to a catheter (not shown). Such a catheter can extend to fluid flow connection with a patient, as known in the art. The outer end of arm tube 36 has a flexible plastic tube 42 inserted therein. Tube 42 can be connected to a reservoir of fluid (not shown) for intravenous administration, as known in the art. The proximal end of trunk tube 34 is occluded by a penetrable, self-sealing resilient septum 45, as known in the art.

With reference now to inner mount tube 30, there is a main cylindrical section 47 having an inner bore 48. Section 47 has an elongated slot 49 extending from its distal opening 50 proximally toward a closed curved end 51. Section 47 has nears its distal end an exterior pair of recessed dimples 52 and 53. Dimples 52 and 53 receive a nub from outer tube 28 as will be described.

Cylindrical section 47 extends proximally toward a thicker proximal section 54. A smaller cylindrical bore 56 extends through section 54 and opens into bore 48 (as seen in FIG. 5). From section 54, tube 30 extends proximally into a frusto-conical lug 60. Lug 60 has an annular groove 63 about its base to receive a locking rim of the outer tube 28, as will be described.

Lug 60 has a proximal funnel-shaped recess shaped to receive and hold as by heat bonding, or by adhesive a frusto-conical portion 66 of a connecting conduit section 69. Conduit section 69 has a main cylindrical portion 71 which extends proximally from portion 66. Portion 71 terminates with an outwardly projecting annular flange 73. Section 69 has a proximal cylindrical bore 76 which extends distally into a conical bore 78. Bore 78 in turn extends distally into a small cylindrical bore 81 that passes through portion 66.

A stainless steel needle 83 has its proximal end fitted securely within a bore at the tip of frusto-conical portion 66, so that the hollow bore of needle 83 is in fluid flow connection with bore 81. Needle 83 telescopically extends through the bore 56 of mount tube section 54. As illustrated in FIG. 5, when inner mount tube 30 is mounted to the junction tube 24, needle 83 penetrates septum 45 and extends within the proximal end of junction trunk tube 34.

Hence, it can be seen that a liquid flow conduit is established through the bores 76, 78 and 81 of connecting section 69, and through the bore of needle 83, to permit liquid to flow from the syringe 26 into trunk tube 34.

Now I turn to a description of the outer tube 28. Outer tube 28 comprises a main cylindrical body 88 which has a distal opening 92. At its proximal end, body 88 has an inwardly extending annular rim 94. A cylindrical bore 96 passes through rim 94 to connect with main bore 90. As can be seen in FIG. 5, when outer tube 28 is mounted to inner tube 30, the locking rim 94 fits within the annular groove 63 beneath lug 60.

Near the lower end of section 88 is an inwardly projecting nub 100 sized to be lockingly but releasably inserted in either one of the dimples 52 or 53 of the inner tube 30.

Outer tube section 88 has an b-shaped slot comprising a longitudinal slot section 104 and a transverse slot section 106. Slot section 104 has a distal opening 108, while slot section 106 terminates in a longitudinal edge 109. The b-shaped slot having sections 104 and 106 has a transverse proximal edge 110. At the distal juncture of slot sections 109 and 106, body 88 has a proximally projecting nib 112. The distance from the proximal end of nib 112 to the closest point of transverse edge 112 is slightly less than the longitudinal section length of junction tube arm 36 at the point of intersection of those parts when the mount tubes 28 and 30 are connected to junction tube 24 as will be described. Since nib 112 is made of a resilient material, it gives way under arm 36 when the mount tube 28 and junction tube 24 are rotated relative to each other by the hands in either direction. Transverse section 106 is therefore divided into two portions, a narrowed portion 114 and an enlarged portion or hollow 116. The hollow 116 is sized to accommodate the length of the major axis of the elliptical section of the arm 36 at the point wherein the arm intersects the body 88 at hollow 112. The hollow is most preferably further of adequate size to receive the different lengths of the major axes of the elliptical sections produced by the variation in branching angles of junction tubes in conventional use.

Mount tube 28 and mount tube 30, including its connecting section 69, can be made of plastic such as polypropylene, or other selected materials. The outer mount tube 28 in particular should be made of a flexible resilient material, such as plastic, so that the nib 112, nub 100 and the proximal lock rim 94 can compress and flex to operate as desired. Although the connecting section 69 has been shown separate from main body 47, body 47 and connecting section 69 can be integral with one another, and molded of the same unitary piece of plastic. Outer tube 28 can be a unitary piece with all the portions integrally connected with each other, and can be of molded plastic.

In assembling the device 22, as it has been described, the connecting section 69 can first be fitted to body 47 with the needle 83 sliding telescopically through bore 56 of proximal section 54, and with the parts secured as before described. The mount tubes 28 and 30 can then be joined by moving inner tube 30 slidingly within bore 90 of outer tube 28, until the outer surface of lug 60 contacts the distal side of lock rim 94.

At this point, inner mount tube 30 can be shoved as by the hands proximally relative to outer tube 28, so that rim 94 flexes in a proximal direction to thus enlarge the opening of bore 96 to allow passage of lug 60. Lug 60 is moved to the point illustrated in FIG. 5, so that the lock rim 94 can flex back to the position shown, to thus lock mount tubes 28 and 30 against longitudinal movement relative to each other. In this FIG. 5 position, the lock rim 94 fits within the groove 63 to permit rim 94 to rotate about lug 60. When the tubes 28 and 30 are mounted, the outer surface of inner tube body 47 is telescopically received within outer tube bore 90 for snug fitting, but yet the fit allows rotation of the tubes 28 and 30 relative to each other.

The outer tube 28 can be positioned relative to inner tube 30 so that inner tube slot 49 is aligned with the outer tube slot section 104, such as illustrated in FIG. 9. Then junction tube 24 can be moved so that the main trunk 34 is longitudinally aligned with inner tube bore 48, and the junction tube arm 36 is aligned with tube slots 49 and 104. Junction tube trunk 34 is slid within inner tube bore 48 to the position shown in FIG. 9, so that the upper surface of junction arm 36 contacts the transverse slot edge 110 of outer tube 28. When this occurs, needle 83 pierces septum 45 and enters within junction tube trunk 34.

In this FIG. 9 position the outer tube nub 100 fits within the dimple 53 (FIG. 11). This locks the two tubes 28 and 30 to each other by a force of low resistance so that the tubes are held in fixed position relative to one another. This locking helps to inhibit non-volitional rotation of the two tubes 28 and 30 relative to one another. Yet the lock of nib 100 with dimple 53 is such that tubes 28 and 30 can easily be rotated by the hand relative to each other.

When the two tubes 28 and 30 are mounted to junction tube 24 as shown in FIG. 9, device 22 can then be moved to a locked position relative to arm 36. This is done by rotating outer tube 28 counterclockwise relative to junction tube 24 and inner tube 30 (from the view looking at FIG. 7) so that junction tube arm 36 slides along b slot edge 110 to compress nib 112 and thence move into the transverse slot 106, such positioning being illustrated clearly in FIGS. 4 and 5. In this position, inner tube section 47 occludes the outer tube slot section 104. A bright color, such as red, or the word "LOCKED" can be provided on the portion of inner tube section 47 which occludes the longitudinal slot section 104. The bright color or "LOCKED" is visible to an observer through slot section 104 when the locked position is achieved.

In this second locked position, nub 100 is received within the dimple 52 of inner tube 30 (FIG. 8). This again helps resist non-volitional rotation of the inner tube 30 relative to the outer tube 28 to help hold the position of FIGS. 4 and 5. The nub 100 projection which narrows the width of slot section 106 thus provides a gate of resistance for passage of the arm 36 to and from slot sections 106 and 104.

In the locked position of FIGS. 4 and 5, the arm 36 extends through a window formed by a proximal part of inner tube slot 49, and by the outer tube slot 106. In this position, longitudinal movement of outer tube 28 relative to junction tube 24 is inhibited by the distal and proximal edges of slot section 106. Since inner tube 30 is secured to outer tube 28, inner tube 28 likewise is longitudinally locked.

In the locked position of FIGS. 4 and 5, transverse movement of arm 36 relative to outer tube 28 is blocked in one direction of rotation by edge 109 of slot section 106. In the other direction of rotation, movement of arm 36 is blocked by the resistance of inner tube section 47 as seen in FIG. 7, which in turn is held in position relative to outer tube 28 by the locking of nub 100 and dimple 52, as seen in FIG. 8. Rotation is also inhibited by nib 112. Hence there is resistance to movement of arm 36 from slot section hollow 116 in every direction of movement.

With device 22 so mounted to junction tube 24, the needle 83 is securely held within tube 24 in fluid flow connection therewith, so that it cannot be knocked or shaken loose by accident.

In such position, the neck 120 of syringe 26, or a connecting member from another secondary fluid source, can be telescopically inserted within the conforming bore 76 of connector 69. Syringe 26 or other secondary fluid source can then be operated as known in the art to force fluid contained therein through the previously described conduit through needle 83 into junction tube trunk 34, to thus be in fluid flow contact with the liquid in trunk 34 and arm 36. After the liquid has been transferred from syringe 26 into junction tube 24 through needle 83, outer tube 28 can then be hand rotated to align inner tube slot 49 with outer tube slot 104. Such hand rotation releases the lock of nub 100 with dimple 52, and moves nub 100 back to dimple 53 as shown in FIG. 11.

Device 22 can then be moved to slide arm 36 through inner tube slot 49 and outer tube slot section 104 to permit complete removal of device 22 from junction tube 24. Device 22 can then be discarded, and junction tube 24 can again be available for receiving a new secondary fluid source.

It can thus be seen that in order to remove arm 36 from slot hollow 116, it is necessary to move outer tube 28 in two different directions relative to arm 36 to move arm 36 from engagement with tube 28. Movement of the tube 28 relative to arm 36 in a single direction, or vice versa, does not disconnect arm 36 from tube 28.

As seen in FIG. 5, hollow 116 has a width to receive the arm 36 extending angularly therethrough.

If desired, the slot having two sections 104 and 106 can be provided in the tube 30, and the single slot 49 can be in tube 28.

The connection of tubes 28 and 30 can also be provided by having the recess corresponding to groove 63 located in tube 28, and the locking projection corresponding to rim 94 extending from tube 30.

For a junction tube having an outer diameter of the septum 45 of 7 mm, and an arm 36 extending at an angle of 35°, with the outside diameter through the cylindrical cross section of the arm 36 being 6 mm, the major axis of a longitutinal section ellipse of the arm 36 being 10 mm, the dimensions of the device 22 can be as follows: the inner tube 30 has an internal diameter of about 8 mm, a width for slot 49 of about 6.5 mm, the cylindrical body 47 has a length of about 55 mm, and a thickness of 0.8 mm. The outer tube 28 has a length of about 58 mm, a thickness of 0.8 mm., the longitudinal slot section 104 has a width of about 6.5 mm, the narrow passage 114 has a width of about slightly less than the major axis of the elliptical section of the arm 36, such as about 8.5 mm, the hollow 116 has a breadth of slightly greater than the major axis of the longitudinal elliptical cross section such as about 10.5 mm. In order to universally accommodate larger septae, the preferred embodiment of device 22 could be slightly larger.

The size of these dimensions can vary with differences in the angle of extension of the arm 36 relative to trunk 34. The more acute the angle of arm 36 relative to trunk 34, the greater the width of the hollow 116 required to accommodate the portion of the arm 36 extending therethrough, and likewise the wider the passage 114.

Because of the combination of the two tubes 28 and 30 and the tolerances achieved thereby, a single design of tubes 28 and 30 can interact with junction arms having a range of angles of extension for arm 36.

For example, the hollow 116 may have a breadth of 11.5 mm and because of the presence of inner tube 30, still securely hold an arm 36 having an angle of extension of 44° and a major axis length of the arm 36 longitudinal section of only 7.5 mm. The ability to securely hold the arm 36 despite considerable differences between such a major axis length and hollow 116 breadth is due to the tightness of fit provided by the inner tube elongated slot 49. This ability provides for the construction of a device 22 which can tightly hold virtually all existing commonly used junctions of the type similar to junction tube 24.

Now I turn to the modification shown in FIGS. 12 and 13. With this design, the outer tube is shown as 130 and the inner tube is shown as 132. In general, with this modification, the means for receiving the liquid from an outside source, such as a receptacle, is mounted with tube 130, and the conduit flow from the receiving means to within the junction tube 24 also extends with the tube 130. The b-shaped slot in tube 130 can be the same as that described for outer tube 28.

More specifically, outer tube 130 has a main cylindrical body 88'. At the proximal end of body 88' is an inwardly extending annular collar 134. Collar 134 has a cylindrical bore extending therethrough that telescopically and snugly receives a receptacle 69'. Heat bonding or adhesive can be used to hold receptacle 69' within the said bore. Receptacle 69' can be the same as that shown as 69. A needle 83' is mounted with receptacle 69' so that the flow channel of needle 83' is in liquid flow connection with the bores 76' and 78' of receptacle 69'. Distal to the collar 134, a resilient angular ring-shaped rib 138 projects inwardly from tube wall 88'. A cavity 140 is formed between rib 138 and flange 134.

The remaining portion of body 88' is similar to that of body 88, with a b-shaped slot having sections 104' and 106' with a nib 112', a hollow 116' and a narrowed slot passageway 114', as well as a slot edge 109'.

The inner tube 132 has a body 47' with a longitudinal slot 49', like that of slot 49, having an opening 50' and an end 51'. Body 47' likewise has dimples 52' and 53' corresponding to the dimples 52 and 53 to receive a locking nub 100' (FIG. 13).

Tube 132 has an interengaging lug 60' having the same shape as lug 60, with an annular groove beneath it for receiving the annular rib 138, as seen in FIG. 13. Tube 132 likewise has a thicker proximal section 54' corresponding to section 54. The needle 83' can pass through a bore 56' during assembly to be described.

In operation, the device 22' can be assembled by aligning the tubes 130 and 132, such as depicted in FIG. 12, and moving tube 132 to fit within the bore 90' of tube 130. Tube 132 is moved so that the exterior surface of frusto-conical lug 60' presses against the resilient annular rib 138 to flex it and enlarge the opening within rib 138 to permit passage of lug 60' therethrough. Lug 60' moves within cavity 140 as shown in FIG. 13. This allows rotation of tube 132 relative to tube 130, but yet longitudinally locks tube 132 to tube 130.

To mount the device 22' to junction tube 24, slot 49' and slot section 104' are aligned with each other as before described, and the junction arm 36 moved to the point near the proximal edge 51' of slot 49' to the FIG. 13 position.

The modification 22' can function similarly to that of the device 22. The outer tube 130 can be rotated relative to the inner tube 132 so that the junction arm 136 moves through the narrow slot passage 114' beyond nib 112' into hollow 116'. In this position, the arm 36 is then bound by the proximal and distal edges of slot section 106' as well as by slot edge 109', and further is confronted by the resistance of nib 112', and the abutment of inner tube 47' against the arm 36 near nib 112' to provide locking engagement. With this position, the arm 36 cannot be disengaged from the device 22' through movement of the arm 36 in a single direction of motion relative to the tube 130.

Rotation of the inner tube 132 can be achieved without rotation of the receptacle 69', in contrast to the design of device 22. This has an advantage in that if the thumb is applied to the arm 36 to force it from slot 104' into the hollow 116', the inner tube 132 moves with the junction tube 24 while the outer tube 130 remains stationary relative to the hand and the junction tube 24. This means that receptacle 69 does not rotate relative to hand movement, and this helps avoid the potential for disengagement of the syringe or other source of fluid, such as a flexible tube, from the receptacle 69' by the force of the hand. This method of moving the arm into the locking engagement with the thumb is very convenient and therefore appears to be a preferable mode of operation.

To remove the arm 36 from the locking engagement within hollow 116', one hand can hold outer tube 130 while the forefinger of the other hand is placed on arm 36 to force it out of hollow 116' into slot section 104' to the FIG. 13 position. Device 22' can be completely removed from junction tube 24 by sliding trunk 24 away from the tubes 130 and 132.

The embodiment in FIGS. 12 and 13 also illustrates how the single member device can operate. In this instance, the tube 130 can be singularly used without the tube 132.

The tube 130, when so used, can be reduced to have an inside diameter such as that shown for the tube 132. The tube 130, with the reduced inside diameter, can then be aligned with junction tube 24 so that the arm 36 can be moved through slot section 104' to abut slot edge 110'. Arm 36 and tube 130 can then be rotated relative to each other to move arm 36 past nib 112' into hollow 116'. In this position, movement of arm 36 is again blocked by the proximal and distal edges of slot section 116' as well as by slot edge 109'. Further, resistance to arm 36 movement is provided by nib 112'. Thus movement in any one direction of motion will not disengage arm 36 from tube 130.

Tube 130 can be disengaged from arm 36 by rotating the two relative to each other to move arm 36 toward the proximal end of slot 104'. Tube 130 can then be slid away from arm 36 to disengage tube 130 from junction tube 24.

The embodiment described using tube 130 as a single member may not fit snugly upon arms which extend at substantially different angles than shown for arm 36 and therefore such a design is less universally applicable and is less preferred than the arrangement 22' which uses both tubes 130 and 132, and the arrangement 22 which uses tubes 28 and 30, which embodiments can fit snugly upon junction arms which extend at varying angles.

An embodiment comprising only tube 30 is additionally useful for engaging junction tube trunk 34 and arm 36 for administration of fluid when a secure locking means is not desired.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A medical device for securing connection of a fluid source with a junction section of a tubing system which can be connected with a patient's blood vessel, the junction section having a trunk section and an arm section branching from the trunk, the said arm section being in liquid flow connection therewith, comprising
    (a) a first member having means for being mounted with the junction tube;
    (b) a second member having means for being mounted in association with the junction tube and in association with the first member so that the second member can rotate relative to the first member and relative to the junction tube, to allow the second member to rotate to and from first and second positions relative to the first member; and
    (c) the second member and the first member having means for allowing the junction tube to be moved away from the first and second members to be disconnected therefrom when the first member and second member are in the first position relative to each other, and means for blocking the junction tube against movement relative to the second member when the first and second members are moved to the second position relative to each other.

2. In the preamble of claim 1, the source of fluid having a conduit:
    and further in the body of claim 1 wherein the device comprises one of the first member or second member having means for receiving the conduit, and means for for allowing liquid flow from the receiving means to inside the junction tube.

3. The medical device of claim 2 wherein the means for allowing liquid flow comprises one of the first member or the second member having a needle associated therewith.

4. The medical device of claim 3 wherein the needle is mounted with the first member, so that when the first member is mounted with the junction tube, the needle extends within the junction tube.

5. The medical device of claim 3 wherein the needle is mounted with the second member, so that when the second member is mounted to the junction tube, the needle extends within the junction tube.

6. The medical device of claim 4 wherein the first member is a tube with a longitudinal axis and wherein the needle extends generally in a longitudinal direction relative to the tube of the first member.

7. The medical device of claim 6 wherein the second member is a tube having generally a longitudinal axis, and wherein the needle is mounted with the second tube to extend generally along the said longitudinal axis.

8. The medical device of claim 2 wherein the means for receiving comprises a receptacle associated with one of the first member or the second member, the receptacle having means for receiving the conduit therein.

9. The medical device of claim 1 wherein the means for the first member being mounted comprises the first member comprising a tube, the tube having an end, and the tube having a slot, the slot having an opening at the end of the tube, the slot being sized to slidingly receive the arm of the junction tube.

10. The medical device of claim 9 wherein the means for mounting the second member comprises the second member comprising a second tube having generally a longitudinal axis, the second tube having a second slot, the second slot having a first section sized to allow the arm of the junction tube to slide therethrough, the second slot having a second section extending generally in a transverse direction relative to the longitudinal axis of the second tube, the second slot section opening into the first slot section.

11. The medical device of claim 10 wherein the first and second slots are positioned so that when the junction tube arm is placed at a selected position within the first slot section of the second slot, the first tube and second tube can be rotated relative to one another so that the second tube and the arm are moved in relation to each other to allow the second slot section to receive the arm so that movement of the junction tube in a longitudinal direction relative to the second tube is blocked.

12. The medical device of claim- 1 wherein the means for mounting the second member in association with the first member comprises means for locking the first member from longitudinal movement relative to the second member and means for allowing rotational movement of the first member relative to the second member.

13. The medical device of claim 12 wherein the means for locking comprises one of the first or second members having an annular recess, and the other of said members having a projection extending therefrom for fitting within the said recess.

14. The medical device of claim 13 wherein the first member has a projection and the annular recess extends about the projection, and wherein the second member has a rim shaped to fit within the recess.

15. The medical device of claim 13 wherein the projection is comprised of resilient material which can bend to permit it to become aligned with the recess for reception therein.

16. The medical device of claim 1 further comprising means for releasably locking the first member relative to the second member when the first and second members are in the second position relative to each other, said locking means being releasable by force of the hand to permit movement of the second member and the first member to the first position.

17. The medical device of claim 16 further including releasable means for locking the first member and second member to one another when those members are in the first position, said means being releasable by hand movement of the first member relative to the second member.

18. The medical device of claim 10 comprising means for holding the arm within the second section of the second slot comprising a nib extending from the second tube into the second section of the second slot, the nib extending into the second slot section a distance making the passageway therethrough less than the width of the corresponding arm section, the nib comprising resilient material so that the arm can enlarge the passageway to allow movement through the passageway when the arm is rotated relative to the second member by the hand to permit the arm to enter the second slot section.

19. The medical device of claim 18 wherein when the arm is with the second slot section beyond the nib, hand rotation of the second tube relative to the arm, or of the arm relative to the second tube, in the direction of moving the arm from the second slot section into the first slot section enlarges the passageway to permit the arm to pass into the first slot section.

20. The medical device of claim 11 wherein the second slot has a general "b" shaped with one slot section extending generally longitudinally relative to the second tube, and the other slot section extending generally transversely to the second tube.

21. A medical device for securing the connection of a liquid source with a junction section of a tubing system which can be connected with a patient's blood vessel, the junction section having a truck section which is substantially straight and an arm section extending at an angle from the trunk and in liquid flow connection therewith, the device comprising:
    a generally elongated tube having a bore for receiving the trunk of the junction tube, the tube having a generally longitudinal slot with an opening for slidingly receiving the arm of the junction tube so that the elongated tube can be moved to fit about the trunk when the arm is aligned with the slot opening and the elongated tube is moved in a generally longitudinal direction relative to the junction tube and
    a second tube coupled to said elongated tube and having a distal end and having a bore sized to receive the first tube, the second tube having a second slot, the said second slot having a first section and a second section, the first slot section having an opening at the distal end of the second tube, the second slot section having an end and having an opening that connects with the first slot section so that the arm can pass from the first slot section into the second slot section, the first and second slots being positioned relative to the first and second tubes, respectively, so that the first and second tubes can be put in a first position to allow the junction arm to be within the first slot and within the first section of the second slot to allow the junction tube to be moved away from the first and second tubes to be disconnected therefrom, and so that the second tube and first tube can be rotated relative to one another to a second position so that the junction tube is blocked from disconnection from the second tube when the junction tube is moved relative to the second tube in any single direction of motion.

22. The medical device of claim 21 further comprising means for locking the first tube and second tube to each other to resist longitudinal movement of the first tube to the second tube but to allow rotational movement of the first tube relative to the second tube, comprising one of the first or second tubes having a recess, and the other of said first or second tubes having a projection for fitting within said recess.

23. The medical device of claim 22 further comprising one of the first or second tubes having a lug, the lug having a proximal end and a distal end, with the lug tapering from a larger cross section at its distal end toward a smaller cross section at its proximal end, with the recess being an annular recess extending about the distal end of the lug.

24. The medical device of claim 23 wherein the means for locking the first and second tubes to one another comprises the second tube having an inwardly extending annular projection received within the said recess, the projection comprising a resilient material that flexes when the lug is pressed against it by hand movement to allow passage of the lug therethrough with the projection received within the annular recess after passage of the lug therethrough.

25. The medical device of claim 21 further comprising the second slot section having a hollow of greater breadth than the major axis of the corresponding section of the arm which intersects with the hollow, the hollow being capable of receiving the arm for locking engagement, the second slot section having a gate to resist movement of the arm from the hollow of the second slot into the first slot.

26. The medical device of claim 24 wherein the gate comprises a nib extending from the second tube into the second section of the second slot to decrease a portion of the passageway of the second slot to be less than the corresponding section width of the arm, the nib comprising resilient material so that the gate can be enlarged when the arm is moved relative to the second tube as the arm moves into and out of the hollow of the second slot to permit passage of the arm to and from the hollow of the second slot section.

27. The medical device of claim 21 further comprising means for receiving liquid from the liquid source comprising a receptacle at the proximal end of the elongated tube.

28. The medical device of claim 27 further comprising a needle connected with the elongated tube, the needle having a bore, and means for providing liquid flow from the receptacle to the needle bore, the needle extending within the junction tube trunk when the tube is mounted to the junction tube.

29. The medical device of claim 26 further comprising means for releasably inhibiting rotation of the first tube relative to the second tube when the arm is in the second section of the second slot, comprising one of the first or second tubes having a projection and the other of said tubes having a recess for receiving the projection, the projection being of resilient material so that the projection can be moved from the recess by hand movement of the first tube relative to the second tube.

30. A releasable locking device for the secure coupling of a source of liquid for patient administration to a junction section of a tubing system, which tubing system can be in liquid connection with a blood vessel, the junction section having a relatively straight portion, the said straight portion further having an adjacent arm in liquid communication therewith extending outwardly from the straight portion of the section, the straight portion having a self-sealing septum present at one end, the device comprising:
    (a) means for providing a first elongated container having a distal and a proximal end,
    (b) a bore extending through the distal end of the container means, the bore being sized to receive the straight portion of the junction section,
    (c) means for securing a needle into the proximal end of said container means so that the needle tip is directed within said bore in an axial orientation toward the distal end of said bore, (d) means for connecting said needle to said source of fluid for patient administration, (e) a longitudinal slot extending along a longitudinal axis from the distal end of the container means toward the proximal end of the container means, the longitudinal slot comprising an opening into said bore, the slot being sized to receive said arm of the junction section, and (f) said container means having means for releasably locking upon said arm after said arm is received into said longitudinal slot including means for providing a second elongated container coupled to said first elongated container having a distal and proximal end, the second container having a main bore extending through its distal end, the bore being sized to receive at least a portion of the first container, the second container further comprising a longitudinal slot extending along a longitudinal axis from the distal end of the second container toward the proximal end of the second container, the longitudinal slot comprising an opening into said main bore of said second container, the slot being sized to receive said junction arm when the first container is received into the main bore of the second container and when the straight portion of said junction section is received into the main bore of the first container, and the second container having means for providing a gate in association with the longitudinal slot in said second container, the gate being capable of receiving the junction arm after the arm has been received into the longitudinal slot of said second container.

31. The structure of claim 30 further comprising the container means having a transverse slot therein, the slot extending at an angle to the longitudinal axis of the container means, the said transverse slot being connected to the longitudinal slot.

32. The structure of claim 31 further having means for connecting the first container means to the second container means when the first container means is received into the main bore of the second container means, said connecting means further having means for retaining the first container means within the second container means.

33. A device for the secure retainment of a needle tip in a position through a resilient septum, the said septum having a direct interface with a flow channel in liquid communication with a blood vessel, the flow channel comprising a cylindrical housing, the device comprising:

(a) an inner elongated containing means having a main bore extending through its distal end, the said bore being sized to receive the septum, (b) an outer elongated containing means coupled to said inner containing means and having a housing, the said housing having an interior wall defining a main bore, the bore being sized to receive at least a portion of the inner containing means, (c) a needle connected to said device, the needle tip extending in an axial orientation within said device, (d) means for locking the inner containing means in a position about the septum when the septum is received into the main bore of the inner containing means to retain the septum within the main bore of the inner containing means and to retain the needle tip in a position extending through the septum, the locking means comprising interaction of the outer containing means about the inner containing means, the locking means further not requiring direct contact between said interior wall of the outer containing means and the housing of said flow channel.

* * * * *